United States Patent [19]

Norén et al.

[11] Patent Number: 5,722,994
[45] Date of Patent: Mar. 3, 1998

[54] IMPLANTABLE HEART DEFIBRILLATOR

[75] Inventors: Kjell Norén, Solna; Pia Hagel, Sollentuna, both of Sweden

[73] Assignee: Pacesetter AB, Solna, Sweden

[21] Appl. No.: 714,310

[22] Filed: Sep. 18, 1996

[30] Foreign Application Priority Data

Sep. 20, 1995 [SE] Sweden ................................ 9503257

[51] Int. Cl.[6] .................................................. A61N 1/39
[52] U.S. Cl. ............................................................ 607/5
[58] Field of Search ............................. 607/5, 6, 7, 8, 607/9

[56] References Cited

U.S. PATENT DOCUMENTS 3,773,050 11/1973 Panico .
4,830,006 5/1989 Haluska et al. .
5,265,588 11/1993 Nelson et al. .

FOREIGN PATENT DOCUMENTS 0 536 873   4/1993   European Pat. Off. .
WO 93/19809 10/1993  WIPO .
WO 95/16495  6/1995  WIPO .

Primary Examiner—Scott M. Getzow
Attorney, Agent, or Firm—Hill, Steadman & Simpson

[57] ABSTRACT

An implantable defibrillator has an electrode lead system a sensing unit for sensing the condition of the heart and emitting a condition signal corresponding to that condition, a control unit for determining the heart's condition from the condition signal and, if a state of fibrillation is present, sending a command signal to a shock pulse generator, which, depending on the command signal, delivers at least one defibrillation shock to the heart via the electrode lead system. The shock being formal of one or more low-energy pulses with an energy less than 2 Joules and a very high voltage, i.e. more than 1,000 Volts. Each low-energy pulse thus has a voltage greatly exceeding the voltage in a conventional defibrillation shock and less energy than the energy in a conventional defibrillation shock.

12 Claims, 4 Drawing Sheets

IMPLANTABLE HEART DEFIBRILLATOR

BACKGROUND OF THE INVENTION

1. Field of the Invention

The present invention relates generally to an implantable heart defibrillator.

2. Description of the Prior Art

A modern automatic implantable defibrillator, such as the one described in Current Problems in Cardiology, Volume XIV, No. 12, Dec. 1989, Chicago, Troup J. P. "Implantable Cardioverters and Defibrillators" (of particularly FIG. 14 on page 699 with accompanying text), incorporates cardioversion and pacemaker stimulation capabilities for both tachycardia and bradycardia and are sometimes referred to as AICD's (automatic implantable cardioverter defibrillators). Defibrillation causes all or at least a sufficient number, of heart cells to depolarize simultaneously by the imposition of a strong electrical field, in the form of an electrical shock, applied across the heart. The electrical shock consists of electrical impulses generated by a pulse generator. The pulses can be delivered to heart in more or less sophisticated spatial and chronological patterns.

Even if opinions sometimes differ, it is usually assumed that the energy for the pulse or pulses in the shock must exceed a certain threshold value in "normal" defibrillation. But the electrical energy required in such "normal" defibrillation according to the prior art is considerable and on the order of 5–40 Joules. The voltage employed is on the order of 700 V, and the duration of the defibrillation pulse is 10–25 ms. The size of the capacitors in the pulse generator is on the order of 150 µF. Tissue subjected to such high-energy shocks run the risk of sustaining damage. For this reason, efforts are being made in the art to reduce the electrical energy required for defibrillation.

SUMMARY OF THE INVENTION

It is an object of the present invention to provide an implantable heart defibrillator wherein the electrical energy required to achieve defibrillation is reduced.

The above object is achieved in accordance with the principles of the present invention in an implantable heart defibrillator having a sensing unit which senses the condition of the heart and which emits a condition signal corresponding to the heart's current condition, a control unit which determines the condition of the heart from the condition signal and which, if a state of defibrillation exists, sends a command signal to a shock pulse generator, the shock pulse generator, dependent on the command signal, delivering at least one defibrillation shock to the heart via an electrode lead system, and the shock pulse generator emitting the defibrillation shock in the form of one or more low-energy pulses having a very high voltage. Each of these low-energy pulses will have a voltage larger than 1000 volts, but an energy content which is less than 2 Joules.

Thus, the defibrillator disclosed herein is based on the discovery in animal experiments that electrical pulses with very high voltage but low energy content, i.e. pulses like the ones which can be generated by static electricity, are capable of terminating fibrillation states in a heart. As noted above, these low-energy pulses have an energy content less than 2 Joules, preferably in the 0.01 to 2 Joules range, and the pulses have a voltage exceeding 1,000 Volts, preferably in the 1,000 to 12,000 Volt range. The duration of a low-energy pulse is in the 1 to 20 µs range, preferably 10–12 µs.

These observations conflict with the prevailing view that high-energy pulses are needed to achieve what was referred to above as "normal" defibrillation. High-voltage pulses with a low energy content have empirically been hitherto assumed to cause only the puncture of membranes of heart cells without causing defibrillation. The view has been that the puncture of cells achieved by such high-voltage pulses is harmful and should be avoided. The aforementioned observation that defibrillation can be achieved with high-voltage, low-energy pulses is therefore surprising in the art.

Thus, the electrical shock delivered by the heart defibrillator according to the invention, i.e. in the form of high-voltage, low-energy pulses, induces defibrillation of the heart, thereby avoiding the aforementioned potentially harmful effect on the heart in conventional defibrillation.

DESCRIPTION OF THE PREFERRED EMBODIMENT

Figure 1:
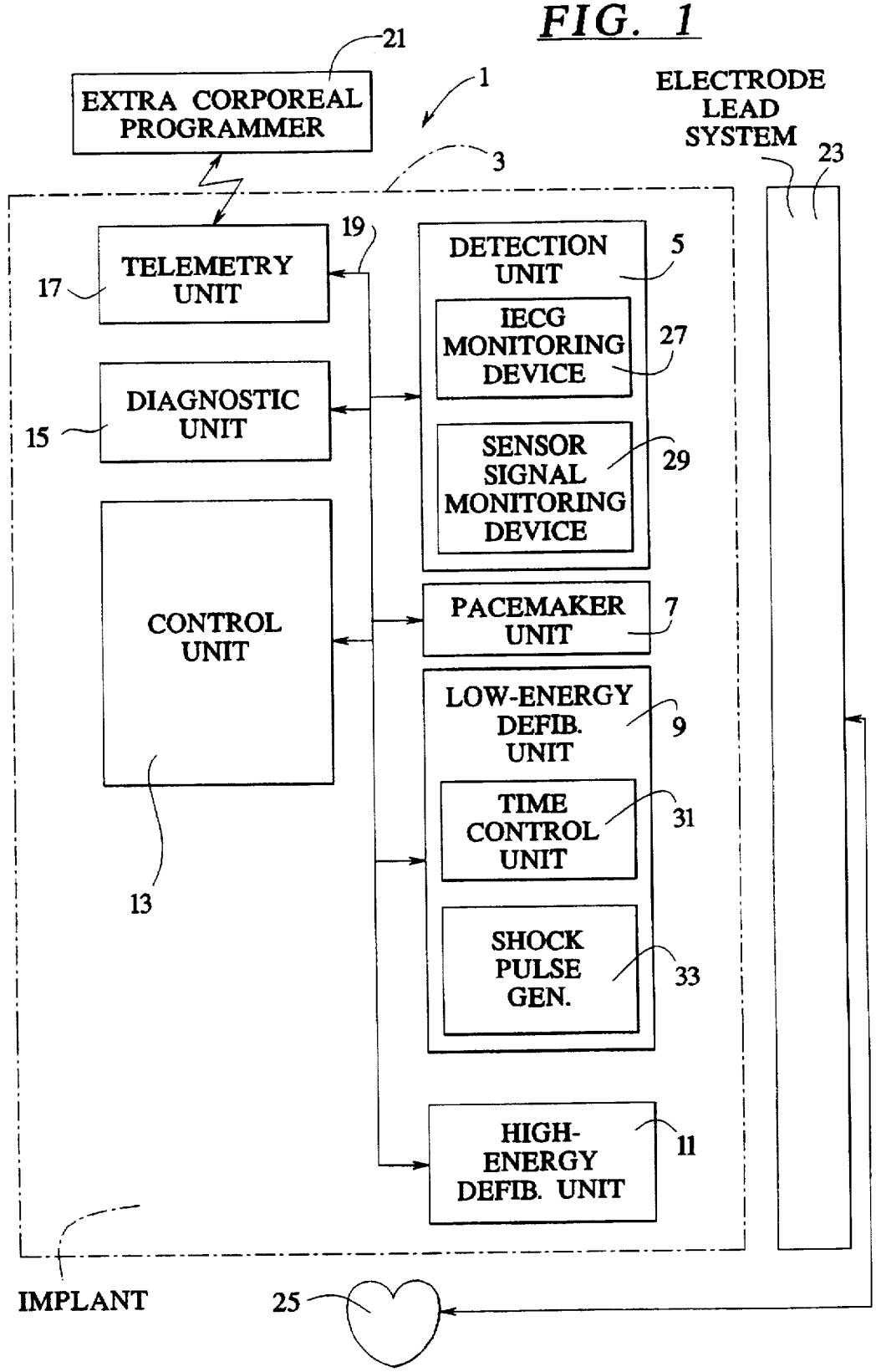
FIG. 1 is a schematic block diagram of a defibrillator according to the invention.

The block diagram in FIG. 1 shows a defibrillator according to the invention. FIG. 1 shows a defibrillator implant 1 whose enclosure can consist e.g. of a titanium capsule 3. The implant 1 contains a detection unit 5, a pacemaker unit 7 capable of supplying stimulation pulses to the heart in both bradycardia and tachycardia, conditions which can develop in both the atrium and the ventricle, a unit for electrical low-energy defibrillation 9, a unit for electrical high-energy defibrillation 11, a control unit 13, a diagnostic unit 15 and a telemetry unit 17. The various units in the implant 1 communicate with each other across a bus 19.

The implant 1 communicates with extra corporeal programmer 21 via the telemetry unit 17, such communications primarily being programming of the implant 1 and transmission of diagnostic data, e.g. on different kinds of events, sensor signals and ECG signals from the diagnostic unit 15.

The implant 1 is connected to a heart 25 via an electrode lead connector 24 connected to a system of electrode leads 23 in order to deliver both pacemaker pulses and shock pulses to the heart, as well as detect signals indicative of cardiac arrest from the heart. The system of electrode leads 23 can include one or a plurality of epicardiac electrodes, i.e. electrodes intended for application to the exterior of the heart, e.g. patch-type or screw-in electrodes. The electrode lead system 23 can also include one or a plurality of endocardiac electrodes, i.e. electrodes intended for placement inside the heart or electrodes intended for placement in the heart's adjacent vessels, alone or in combination with epicardiac electrodes. These endocardiac electrodes can be located both in the atrium and in the ventricle and can be screw-in electrodes, electrodes designed for anchoring with tines or hooks and electrodes containing a ring or an elongate section of conductive material on the electrode lead. The ring or elongate section does not have to be anchored in the heart wall or the wall of a blood vessel. The endocardiac electrodes can be electrodes for both normal heart stimulation and for defibrillation with high or low energy.

It should be noted that FIG. 1 is only schematic, and signals indicating the condition of the heart 25 also encompass signals from measurements of physiological variables, such as the partial pressure of oxygen ($pO_2$) in the blood, at other locations in the body.

According to the above description, the defibrillator implant 1 also incorporates the functions found in a modern defibrillator (AICD) of the kind initially described, in addition to the low-energy defibrillation unit 9 which will be described in detail below. The detection unit 5 monitors the state of the heart with an IECG-monitoring device 27 and a sensor signal-monitoring device 29 for the purpose of detecting normal sinus rhythm or abnormal heart conditions requiring therapy, such as bradycardia, hemodynamically stable/unstable tachycardia, atrial and ventricular arrhythmias and Ventricular fibrillation.

Data from the detection unit 5 in the form of a condition signal is sent to the control unit 13 which, e.g. depending on this signal, orders the requisite therapy, tachycardia-terminating stimulation, and sends a command signal to at least one of the units 7, 9, 11, i.e. to the pacemaker unit 7 in the exemplified tachycardia-terminating stimulation. Thus, the low-energy defibrillator 9 can be used as the only therapy or combined with one or both of the units 7 and 11.

The parts and functions of the defibrillator implant 1 hitherto described are, as noted above, conventional in nature and will henceforth only be addressed to the extent that they are related to the low-energy defibrillator unit 9 (henceforth referred to as the defibrillator) which will now be described.

The unit 9 with the low-energy defibrillator consists of a time control unit 31 and a shock pulse generator 33 for high-voltage. The time control unit 31 causes the pulse generator 33 to emit the desired pulses pulse sequences or, alternately, continuous output signals to be emitted by the defibrillator 9. The pulse generator 33 supplies the electrode lead system 23 with sufficient energy to deliver the desired high-voltage, low-energy pulses.

The duration of a low-energy pulse is in the 1 to 20 μs range, preferably 10 to 12 μs. Pulses are emitted one at a time but can be repeated when necessary. A pulse displays a rapid, exponential rise with a rise time on the order of 0.1 μs and an equally rapid, exponential fall time of the same magnitude. These low-energy pulses have an energy content less than 2 Joules, preferably in the 0.1 to 2 Joules range, and pulses have a voltage exceeding 1,000 Volts, preferably in the 1,000 to 12,000 Volt range. The pulse current is on the order of 100 A.

In the emission of voltages up to a maximum of 1,000 Volts, which roughly corresponds to the peak voltage used in conventional implantable defibrillators, some kind of oscillator is used which emits an alternating current which is then stepped up by a transformer with a very large number of windings. Different kinds of passive voltage multipliers can be used to increase the voltage level even further. They consist of a network of capacitors and diodes devised according to a technique familiar to anyone well-versed in the art.

Figure 2:
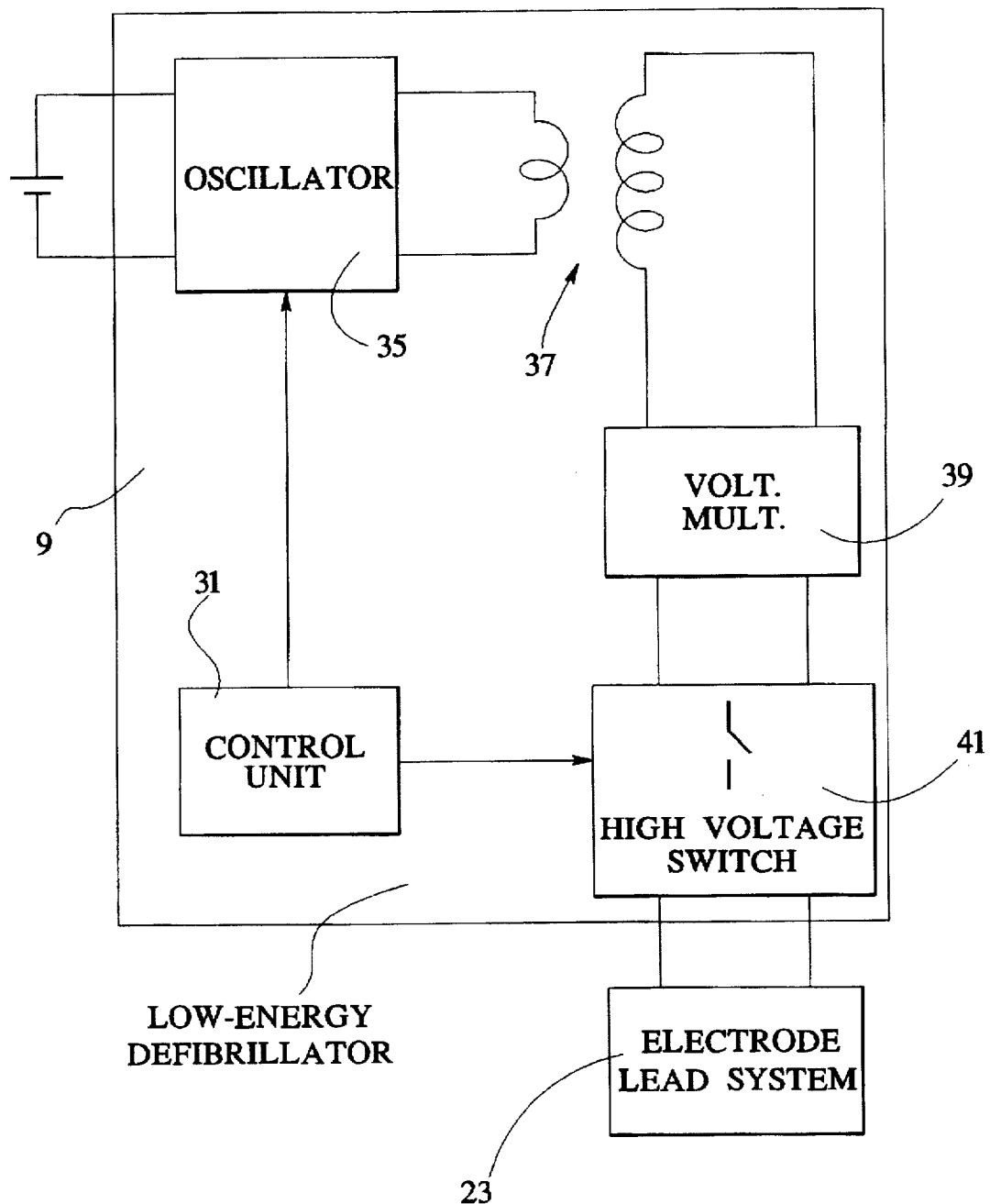
FIG. 2 is a schematic block diagram of a shock pulse generator in the defibrillator according to the invention.

FIG. 2 is a unit diagram of the low-energy defibrillator 9 which contains an oscillator 35 connected to the defibrillator implant's 1 battery voltage, a transformer 37, a voltage multiplier 39 and a high-voltage switch 41. The oscillator 35, transformer 37, voltage multiplier 39 and high-voltage switch 41 jointly constitute the shock pulse generator 33.

The output signal of the oscillator 35 is a an alternating voltage with a peak-to-peak value of about 3 Volts. This voltage is then stepped up in the transformer 37 to a peak-to-peak voltage which could amount to e.g. 1,000 Volts (cf. FIG. 3).

Figure 3:
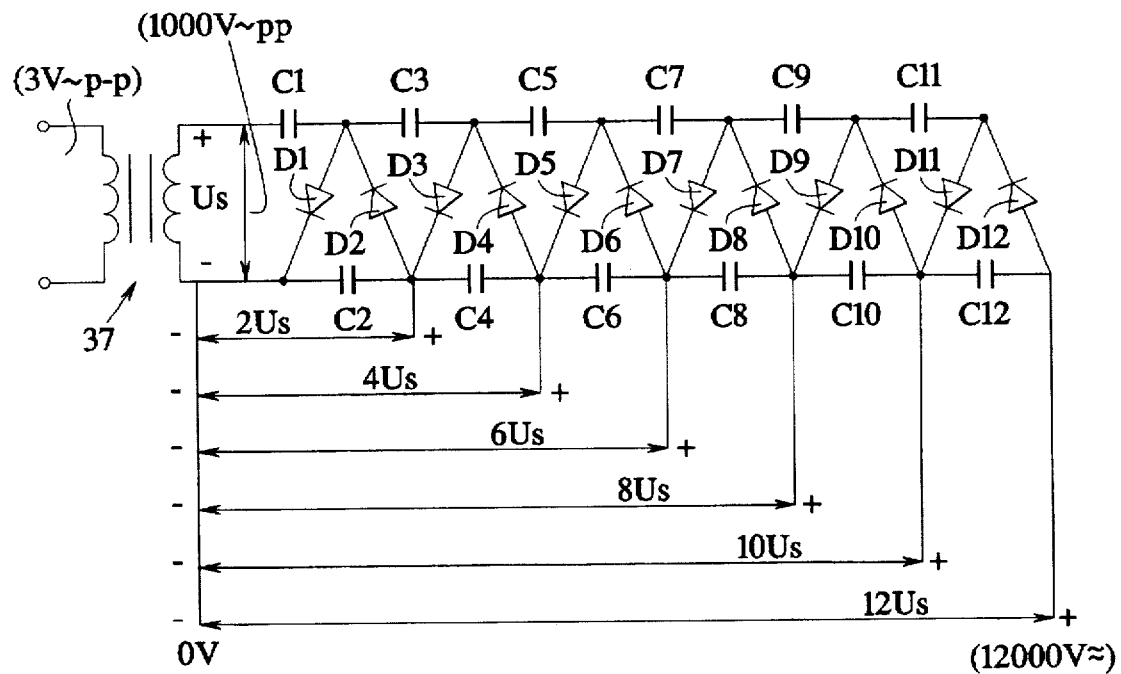
FIG. 3 is a circuit diagram of a voltage multiplier in the shock pulse generator of FIG. 2.

FIG. 3 is a schematic depiction of the voltage multiplier 39 used in the shock pulse generator 33. The voltage multiplier 39 is constructed according a well-known voltage multiplication principle familiar to those skilled in the art. The input signal to the voltage multiplier 39 is the stepped-up alternating current generated by the transformer 37, and the output signal is a high-voltage direct current which is an even multiple of the input signal's peak-to-peak value. The voltage multiplier consists of a pre-defined number of diodes D1–D12 and a pre-defined number of capacitors C1–C12, the number (set at 12 in the FIG.) of diodes and capacitors depending on the output voltage to be generated. According to the embodiment in FIG. 3, the voltage multiplier 39 has two rows of capacitors C1, C3 ... C11 and C2, C4 ... C12, connected in series, one side of the capacitors C1 and C2 being connected to the transformer 37.

The diodes D1–D12 interconnect the rows of capacitors when D1 is connected in its forward direction from the point at which C2 connects to the transformer 37 to a point between C1 and C3. D2 is connected in its forward direction from this point to a point between C2 and C4. D3 is connected in its forward direction from this point to a point between C3 and C5 etc. according to the same principle until the circuit is closed with D12 connected in its forward direction between C11 and C12. The FIG. shows that even multiples of the input voltage's peak-to-peak value can be tapped across all or part of the C2–C12 row of capacitors. The embodiment of the voltage multiplier 39 shown in FIG. 3 increases the peak-to-peak voltage Us from the secondary side of the transformer 37 in six stages to a DC voltage which is twelve times this level, 12Us. For those skilled in the art, it is obvious how this network can be simplified or expanded to achieve different voltage levels. Control of the output voltage level of the voltage multiplier 39 is performed most simply on the primary side of the transformer 37.

The peak voltage across any of the components in the voltage multiplier 39 (capacitors and diodes) is twice the peak-to-peak voltage on the secondary side of the transformer 37. In this exemplary embodiment example, which uses a peak-to-peak voltage of 1,000 Volts on the secondary side, the peak voltage across any component is about 2,000 Volts. None of the components is therefore subjected to the peak output voltage, which is an advantage with this type of circuit. As a result, utilization of practical, physically small components becomes possible, a prerequisite for their use in an implanted device.

Switching the high voltage, generated in the voltage multiplier 39, to the patient for defibrillation is performed according to the invention with a high-voltage switch 41. See FIG. 2. Two different embodiments of this switch will be described in greater detail, referring to FIGS. 4 and 5. In these FIGS. the designation HV (high voltage) refers to the output signal from the voltage multiplier 39. In FIG. 3, HV corresponds to one of the designations 2Us, 4Us ... 12Us.

Figure 4:
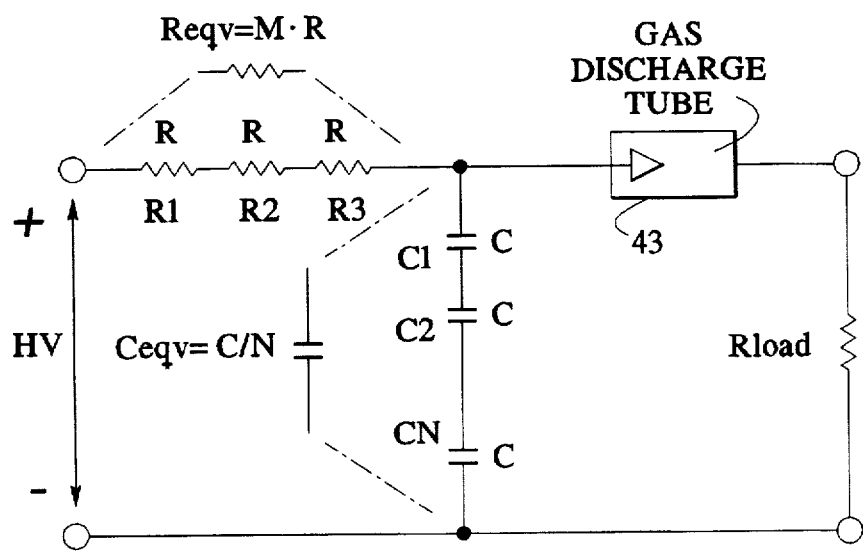
FIG. 4 is a circuit diagram of a first preferred embodiment of a high-voltage switch in the defibrillator according to the invention.

FIG. 4 shows a high-voltage switch 41 according to a first preferred embodiment of the heart defibrillator according to the invention. This switch includes a gas discharge tube 43 as the active element. Tubes are available with ignition voltages from e.g. 250 Volts to 20,000 Volts. In the extinguished state, the tube has an extremely high impedance, i.e. 100 MOhms to 10,000 MOhms. When the voltage exceeds the ignition voltage, an arc ignites very rapidly (in less than 0.1 μs), and large currents are allowed to pass. The voltage across the gas discharge tube 43 is generated through an RC network consisting of an N number of capacitors C1-CN, connected in series, and an M number of resistors R1-RM, connected in series, with an equivalent capacitance Ceqv which is C/N and an equivalent resistance Reqv which is M_R. The series resistance Reqv must be much greater than the load Rload (the patient). Typical values for Reqv and Ceqv are 10 Mohms and 250 nF respectively.

One advantage of this high-voltage switch is that no control input terminal is needed. The voltage across the gas discharge tube is raised until the pre-defined ignition voltage is reached. Discharge then takes place. The type of high-voltage switch described above can obviously be used, with appropriately selected components, for switching a high-energy defibrillation pulse in the high-energy defibrillation unit 11.

Figure 5:
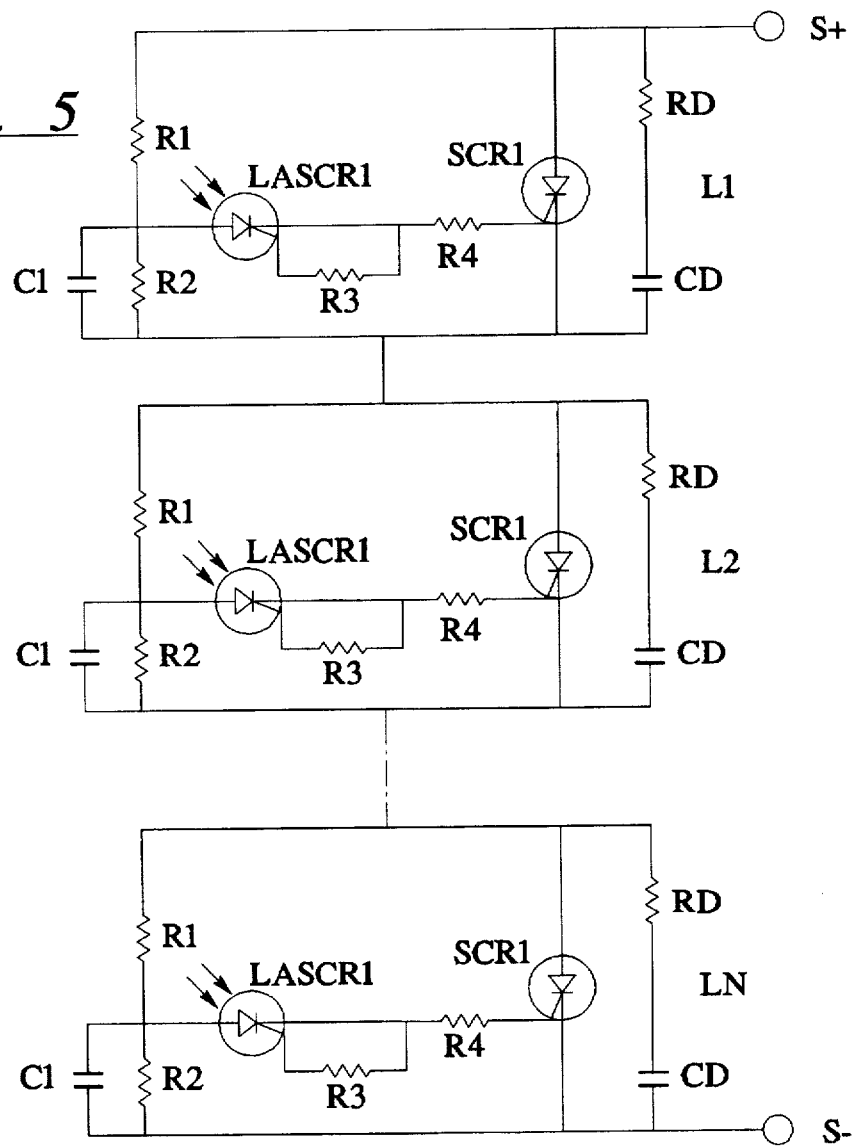
FIG. 5 is a circuit diagram of a second preferred embodiment of a high-voltage switch in the defibrillator according to the invention.

FIG. 5 shows the high-voltage switch 41 in FIG. 2 according to a second preferred embodiment of the heart defibrillator according to the invention. Here, the switch consists of an N number of identical sub-circuits L1-LN, connected in series, with a main thyristor SCR1 (silicon-controlled rectifier) in each sub-circuit. The series-connected sub-circuits L1-LN divide up the total voltage evenly. The voltage across each thyristor SCR1 can be e.g. 1,000 Volts.

Activation of the switch creates a special problem. When activation is by optical means, e.g. with a photosensitive thyristor LASCR1 (light-activated silicon-controlled rectifier), phototransistors can also be used, thereby eliminating galvanic contact with the switch at activation. The arrows at LASCR1 in the FIG. indicate the entry of light and activation of these components. When they become active, they trigger, in turn, the main thyristors SCR1 for switching the high-voltage. A low-voltage LASCR1 can be used if the resistor R1 has a value much greater than the resistor R2. In practice a small flash tube is used as the optical trigger, and fiber optic conductors carry the flash light to each LASCR1. This provides electrically insulated control of the switch. It is also important for the LASCR1 switches to be matched so they are activated simultaneously and protected against high-frequency transients. For this purpose, a number of other components (R3, R4, RD, C1, CD) are included in the circuit schematic but not discussed here, since they do not constitute a direct part of the invention. The FIG. also shows two connection points (S+,S−).

Figure 6A:
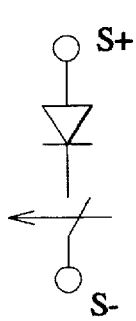
FIGS. 6a–6c respectively show possible positions for the high-voltage switch according to the second embodiment.
Figure 6B:
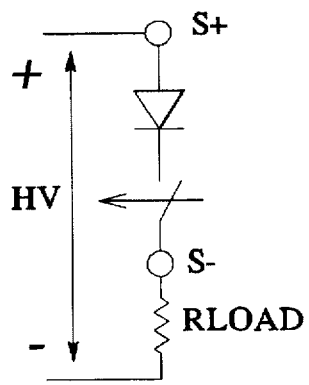
Figure 6C:
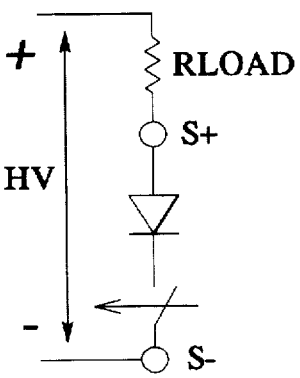

FIG. 6a shows a simplified schematic of the high-voltage switch 41 according to the second preferred embodiment, and FIGS. 6b and 6c show the switch 41 connected to the output signal HV from the voltage multiplier 39 with possible connections of the load Rload (the patient).

Although modification and change may be suggested by those skilled in the art, it is the intention of the inventor to embody within the patent warranted hereon all changes and modification as reasonably and properly come within the scope of their contribution to the art.

We claim as our invention:

1. An implantable heart defibrillator for use with an electrode lead system, comprising:

an electrode lead connector connectable to said electrode lead system;

sensing means connected to said electrode lead connector for sensing a condition of a heart and for emitting a condition signal identifying said condition;

control means for determining the condition of the heart from said condition signal and for identifying whether a state of fibrillation exists and for emitting a command signal if said state of fibrillation exists; and shock pulse generator means, supplied with said command signal and connected to said electrode lead connector, for emitting at least one defibrillation shock to said electrode lead connector upon receipt of said command signal, comprised of at least one low-energy pulse having an energy content of less than 2 Joules and having a high voltage greater than 1000 volts.

2. An implantable heart defibrillator as claimed in claim 1 wherein said shock pulse generator means comprises means for emitting said at least one defibrillation shock having a duration in a range from 1 through 20 microseconds.

3. An implantable heart defibrillator as claimed in claim 1 wherein said shock pulse generator means comprises means for emitting said at least one defibrillation shock having a duration in a range from 10 through 12 microseconds.

4. An implantable heart defibrillator as claimed in claim 1 wherein said control means includes timer means for generating a first timer signal and a second timer signal, and wherein said shock pulse generator means comprises:

a transformer having a primary side and a secondary side;

oscillator means, connected to said primary side of said transformer and supplied with said first timer signal, for developing a primary voltage at said primary side upon receipt of said first timer signal;

multiplier means, connected to said secondary side of said transformer, for multiplying a secondary voltage, produced by said primary voltage, to obtain said high voltage; and a high voltage switch, supplied with said second timer signal and connected between said multiplier means and said electrode lead connector for discharging said high voltage from said multiplier means to said electrode lead system upon receipt of said second timer signal.

5. An implantable heart defibrillator as claimed in claim 4 wherein said high voltage switch comprises a gas discharge tube.

6. An implantable heart defibrillator as claimed in claim 4 wherein said timer means comprises means for emitting said second timer signal as an optical signal, and wherein said high voltage switch comprises a thyristor and a phototransistor connected to said thyristor for triggering said thyristor upon receipt of said optical signal.

7. An implantable heart defibrillator as claimed in claim 4 wherein said timer means comprises means for emitting said second timer signal as an optical signal, and wherein said high voltage switch comprises a light-activated thyristor which is triggered upon receipt of said optical signal.

8. An implantable heart defibrillator as claimed in claim 1 further comprising:

pacing means for emitting pacing pulses to said electrode lead connector and defibrillation means for emitting high-energy defibrillation shocks having an energy content of approximately 40 Joules; and said control means comprising means for selectively activating said pacing means and said defibrillation means for interaction with said low-energy shock pulse generator means.

9. An implantable heart defibrillator comprising:

an electrode lead system;

sensing means connected to said electrode lead system for sensing a condition of a heart and for emitting a condition signal identifying said condition;

control means for determining the condition of the heart from said condition signal and for identifying whether a state of fibrillation exists and for emitting a command signal if said state of fibrillation exists; and shock pulse generator means, supplied with said command signal and connected to said electrode lead system, for emitting at least one defibrillation shock upon receipt of said command signal to said heart via said electrode lead system comprised of at least one low-energy pulse having an energy content of less than 2 Joules and having a high voltage greater than 1000 volts.

10. An implantable heart defibrillator as claimed in claim 9 wherein said electrode lead system includes at least one epicardial electrode.

11. An implantable heart defibrillator as claimed in claim 9 wherein said electrode lead system comprises at least one endocardial electrode.

12. An implantable heart defibrillator as claimed in claim 9 wherein said electrode lead system comprises at least one endocardial electrode and at least one epicardial electrode.

* * * * *